United States Patent [19]
Sigelmann

[11] 4,014,650
[45] Mar. 29, 1977

[54] ULTRASONIC COAGULATION TIMER
[75] Inventor: Rubens A. Sigelmann, Seattle, Wash.
[73] Assignee: Research Corporation, New York, N.Y.
[22] Filed: Apr. 25, 1975
[21] Appl. No.: 571,507
[52] U.S. Cl. .......................... 23/230 B; 23/253 R; 73/64.1
[51] Int. Cl.² .................................... G01N 33/16
[58] Field of Search .......... 73/64.1, 53, 552, 61 R, 73/67.7, 67.8 R; 23/230 B, 253 R
[56] References Cited
UNITED STATES PATENTS

| | | | |
|---|---|---|---|
| 3,040,562 | 6/1962 | Fitzgerald et al. | 73/67.7 X |
| 3,520,659 | 7/1970 | Steinberg et al. | 23/230 B |
| 3,553,636 | 1/1971 | Baird | 73/552 X |
| 3,572,099 | 3/1971 | Wieczorek | 73/67.7 |
| 3,654,072 | 4/1972 | Massa | 73/53 X |
| 3,658,480 | 4/1972 | Kane et al. | 73/64.1 X |
| 3,710,615 | 1/1973 | Johnson et al. | 73/61 R |
| 3,791,200 | 2/1974 | Hayre | 73/61 R X |

*Primary Examiner*—Richard C. Queisser
*Assistant Examiner*—Joseph W. Roskos
*Attorney, Agent, or Firm*—Seed, Berry, Vernon & Baynham

[57] ABSTRACT

A system for measuring the coagulation time of plasma or whole blood. A solution containing the blood sample is irradiated with pulsed ultrasound, and the back-scattered ultrasound is continuously measured. A predetermined quantity of thrombin is then added to the solution, causing the amplitude of the backscattered ultrasound to fluctuate until coagulation occurs. The elapsed time between the addition of thrombin and the inception of coagulation is the coagulation time, and is an indication of the concentration of fibrinogen in the blood sample.

17 Claims, 8 Drawing Figures

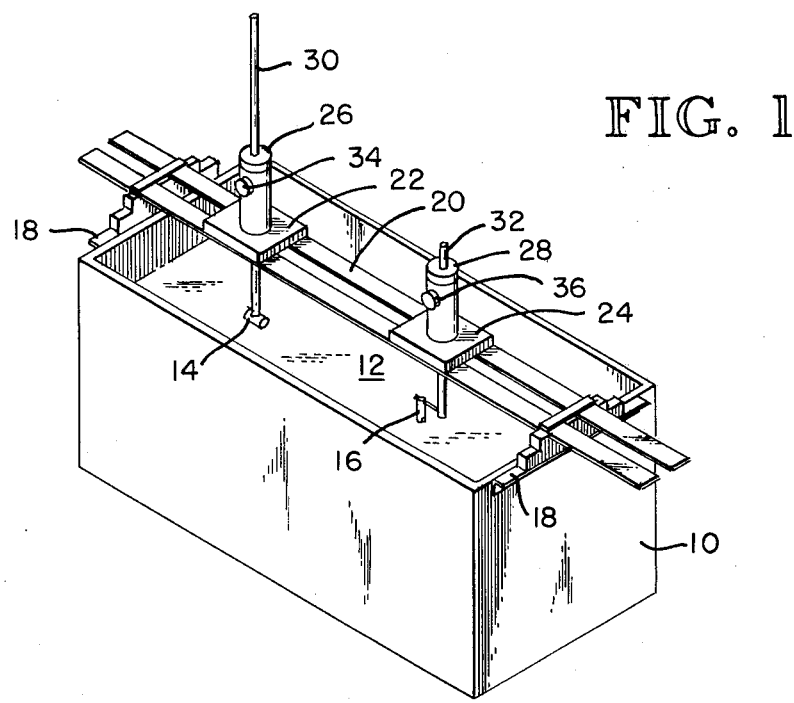
FIG. 1
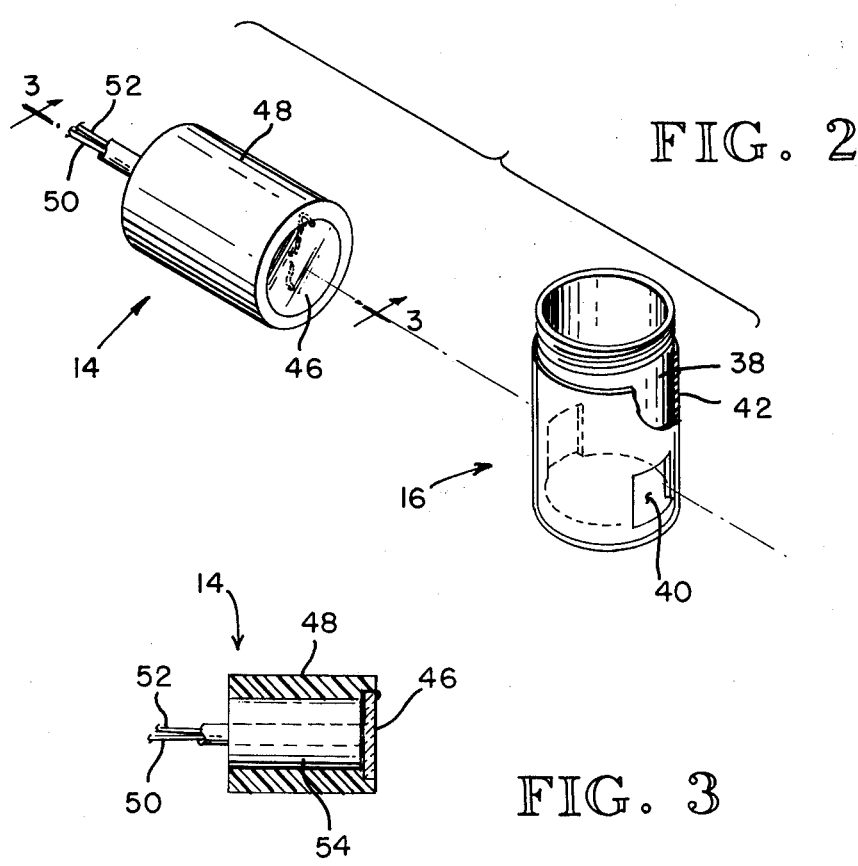
FIG. 2
FIG. 3

ULTRASONIC COAGULATION TIMER

The invention described herein was made in the course of work under a grant or award from the Department of Health, Education and Welfare.

BACKGROUND OF THE INVENTION

1. Field of the Invention

This invention relates to systems for performing hematological tests and, more particularly, to a system for measuring the coagulation time of plasma or whole blood by measuring the ultrasound backscattering characteristics of the plasma or whole blood.

2. Description of the Prior Art

Blood, when drawn from the blood vessels of a living body, is perfectly fluid. In a short time, it becomes viscid, and this viscosity increases rapidly until the whole mass of blood forms a clot. The essential substances in the blood necessary for this phenomena to occur are: (1) prothrombin, (2) calcium salts, (3) fibrinogen, and (4) tissue extract. The first three substances are in solution in the blood plasma. Tissue extract is set free by crushed tissue cells. Prothrombin may be converted to active thrombin by the action of calcium, but in the circulating blood, this is prevented by antithrombins. These antithrombins must first be neutralized by the tissue extract. Then the calcium reacts with the prothrombin to form thrombin, which, in turn, reacts with the fibrinogen to form fibrin. Initially, a fibrin monomer is formed, but subsequently the fibrin polymerizes to form a clot. The length of time required for the coagulation process is a function of the chemical characteristics of the blood sample. The concentration of fibrinogen in a sample of plasma or whole blood may be measured by adding a predetermined quantity of thrombin to the plasma and recording the time required for the fibrinogen to be converted to fibrin and form a clot. In the conventional thrombin time test, 0.2 ml of a solution of citrated plasma is mixed with 0.1 ml of thrombin solution at 37° C. For normal plasma samples, a fibrin clot is formed in 15 to 20 seconds. However, the thrombin time is prolonged by traces of antithrombins, such as heparin, by pathological fibrinogens, by the presence of fibrin degradation products as a consequence of increased fibrinolysis, and by very low or very high fibrinogen concentrations in the plasma. The measurement of thrombin time is, therefore, a simple, but highly significant clinical assay.

Presently, the detection of a fibrin clot is based on two principles. One principle utilizes the lower electrical conductivity of fibrin with respect to fibrinogen. The plasma containing the fibrinogen is collected in a vibrating electrode which measures its conductivity. A marked decrease in the conductivity indicates that a fibrin clot has formed. A significant disadvantage of this method as conventionally practiced is that whole blood may not be used. Instead, it is first necessary to centrifuge the blood to separate the plasma therefrom.

The other principle for measuring the thrombin time makes use of the change in the optical absorption during the coagulation process. Fibrin has a higher coefficient of absorption than fibrinogen. Thus the transmission of light decreases during the coagulation process when fibrinogen is converted to fibrin by the addition of thrombin. As with the conductivity principle, this method for measuring the thrombin time must be performed with plasma since whole blood is too opaque and does not provide enough transmission. Thus the whole blood must first be centrifuged to obtain the plasma. The centrifuging necessary to perform thrombin time tests using present methods increases the cost of determining the thrombin time for a sample of blood and increase the time required to obtain the results of the test.

Recent technological developments in the field of medicine have greatly improved the available medical care. At the same time, the extensive use of procedures and instrumentation that have stemmed from these developments has added significantly to the cost of medical care. Therefore, there is considerable interest in procedures and methods for automating and reducing the cost of medical care. In particular, ultrasound is now extensively used in medicine. Therapeutical devices, such as heat generators, Doppler-flow meters and imaging systems, are a few examples of such uses. However, ultrasound has not yet been used in the hematological laboratory.

SUMMARY OF THE INVENTION

It is an object of the invention to provide a system capable of measuring the coagulation time of whole blood, thereby avoiding the need to centrifuge the blood to obtain plasma.

It is another object of the present invention to provide a quick, accurate and inexpensive coagulation timer.

It is a further object of the invention to devise a system for furnishing continuous information during the formation of a clot, thereby providing an indication of pathological coagulation.

It is still another object of the present invention to provide a technique for measuring coagulation time which is applicable, with appropriate modifications, to a wide variety of hematological tests and biochemical reactions.

It is a still further object of the invention to provide a system for measuring the fibrinogen concentration of whole blood automatically, without the necessity of an operator for measuring and evaluating the ultrasound backscattering.

These and other objects of the present invention are accomplished by providing a system for irradiating a sample of whole blood or blood plasma with ultrasound and measuring the ultrasound backscattering characteristics of the sample in response to the addition of a predetermined amount of thrombin. Upon addition of the thrombin, the sample produces backscatter amplitude fluctuations which markedly decrease upon coagulation of the sample. The amplitude fluctuation in the backscattering is due to the turbulence caused by dropping the thrombin into the blood or plasma solution and by the formation of fibrin monomer. As the fibrin polymerizes, the fluctuation decreases and ultimately stops. If the concentration of fibrinogen is low, the probability that the monomer will polymerize is small and the clot may not form or, if it forms, may break down. In either case, the backscattered signal will not stabilize. By examining the rate at which the fluctuations cease, defective polymerization of the fibrin can be detected. For normal blood samples, the fluctuation end point should be relatively clear. A fuzzy or indefinite end point is thus an indication of pathological coagulation. The length of the period during which the fluctuations occur provides a measurement of the fibrinogen concentration in the sample, and the fluctuation waveform provides an indication of the presence of anticoagulants and pathological fibrinogens.

Means are also provided for continuously recording the backscattered ultrasound signal during formation of the clot. The characteristics of this signal provide relevant information in cases of pathological coagulation.

BRIEF DESCRIPTION OF THE DRAWINGS

FIG. 1 is a perspective view of the apparatus for transmitting ultrasound to the blood sample and for receiving the backscattered ultrasound.

FIG. 2 is a perspective view of the ultrasound transducer in a configuration for irradiating the sample holder in which the blood sample is placed and for receiving the backscattered ultrasound.

FIG. 3 is a cross-sectional view of the ultrasound transducer taken along the line 3—3 of FIG. 2.

DETAILED DESCRIPTION OF THE INVENTION

Figure 4:
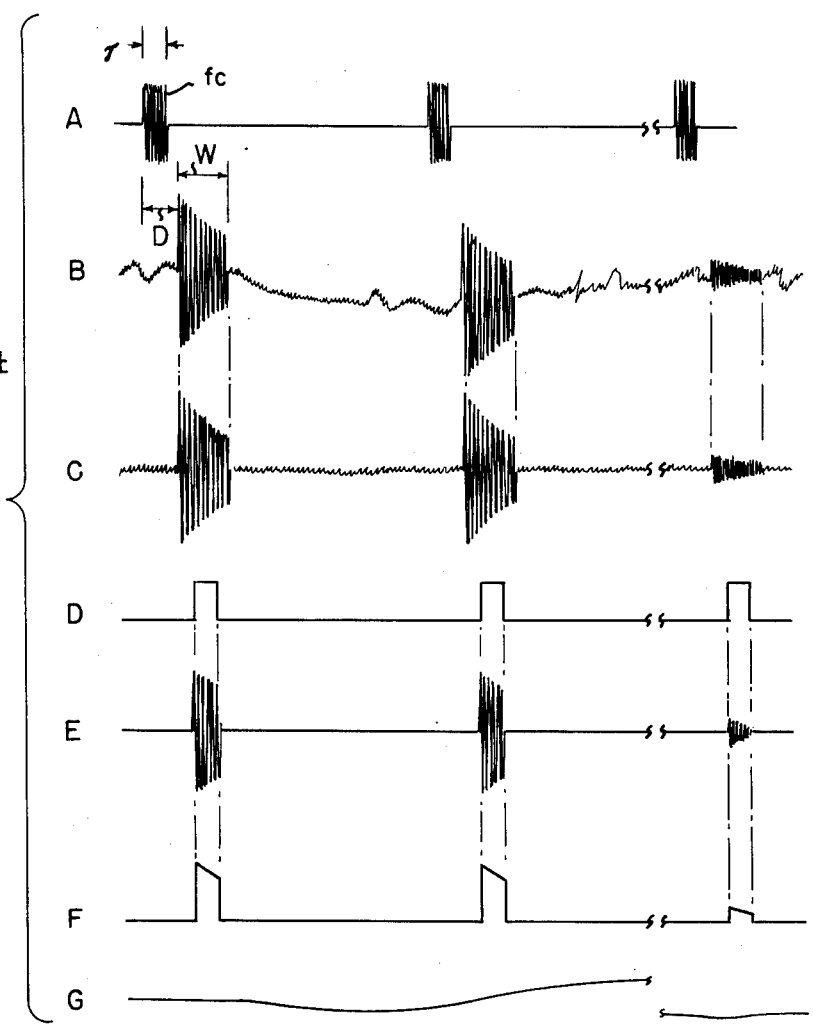
FIG. 4 is a timing diagram illustrating the electrical signal at various points in the system shown in FIG. 5.

Referring to FIG. 1, a tank 10 containing water 12 is used to provide a conduction medium from a transducer 14 to a sample holder 16. It should be noted that other conduction mechanisms not using water are also contemplated. For example, a unitary transducer/sample holder may be used which will eliminate the necessity of providing a medium to conduct ultrasound between the transducer and sample holder. A conventional temperature regulating apparatus (not shown) is provided for maintaining the temperature of the water 12 in the tank 10 at a relatively constant temperature, thereby maintaining the temperature of the contents of the sample holders 16 at the same relatively constant temperature. Secured to the tank 10 by brackets 18 is a graduated track 20 along which a transducer support 22 and a sample holder support 24 are adapted to slide. The track 20 and holders 22, 24 allow the distance between the transducer 14 and the sample holder 16 to be adjusted to correspond to a predetermined delay in detecting the transmitted ultrasound.

The top surface of each of the holders 22, 24 contains a bore over which cylindrical clamps 26, 28 are coaxially secured. Rods 30, 32 are inserted through the bores of the cylindrical clamps 26, 28 and their vertical positions are fixed by thumbscrews 34, 36.

The transducer 14 and sample holder 16 are shown in detail in FIG. 2. The sample holder comprises a tubular plastic container 38 having an open top and a closed bottom. A pair of aligned apertures 40 are cut through the walls of the container 38 adjacent the bottom. The entire container 38 is then covered with a thin rubber membrane 42 which presents a transparent surface to the ultrasound, thereby allowing the ultrasound to irradiate the material in the sample holder through the aperture 40. The transducer 14, which is further illustrated in FIG. 3, is of the piezoelectric type. These transducers are well known in the art. The circular planar piezoelectric ceramic for such transducer can be purchased from the Clevite Corp. of Bedford, Ohio. The transducer 14 is fabricated by fitting a circular planar piezoelectric ceramic 46 into the end of an epoxy tube 48. The epoxy tube 48 is approximately 1 inch long and 0.375 inch in diameter. A pair of leads 50, 52 are then bonded to opposite faces of the piezoelectric ceramic 46. The leads extend axially through the epoxy tube and exit therefrom at the rear. The inside of the epoxy tube is potted with epoxy.

In operation, the height of either the transducer 14 or the sample holder 16 is adjusted by loosening either thumbscrew 34 or 36 and sliding rod 30 or 32 with respect to cylindrical clamp 26 or 28 until the ultrasound beam from the transducer 14 is centered on the aperture 40 of the sample holder 16. The transducer 14 is then driven with the waveform shown in FIG. 4A. The frequency $f_c$ of the ultrasound is not critical, and in one operational embodiment of the invention, 12 MHz is used. A higher frequency will provide more ultrasound scattering. However, as frequency rises, attenuation also increases. The width of the ultrasound burst $\tau$ is, in a preferred embodiment, approximately equal to the time in which sound travels the width of the sample holder 16. Thus, the first cycle of the ultrasound burst reaches the far side of the sample holder at the same time the final cycle of the burst reaches the near edge of the sample holder 16. At this point, the entire sample is irradiated with ultrasound. For a sample holder having a diameter of 0.6 cm, the width of the burst $\tau$ will be approximately 4 $\mu s$. As will be explained hereinafter, the amplitude of each backscatter signal produced by each ultrasound burst is measured separately. Thus, the repetition rate of ultrasound bursts will depend upon the frequency at which samples are desired. This frequency will be a function of the rate at which the amplitude of the backscattering fluctuates. Higher fluctuation frequencies will require more frequent sampling. It has been found that the fluctuations in ultrasound backscattering from a sample of whole blood or plasma upon the addition of thrombin is in the neighborhood of 1 Hz. Thus, a burst repetition rate of 1,000 bursts per second will provide 1,000 measuring points for each fluctuation. The maximum repetition rate of bursts is preferably limited by the round-trip transit time from the transducer to the sample and back to the transducer in order to prevent multiple responses to a single transmission. For example, where the sample holder is 30 cm from the transducer, the round-trip transit time will be approximately 420 microseconds. Thus, for this configuration of transducer and sample holder, an ultrasound burst repetition frequency of substantially greater than 2,000 pulses per second will not be desirable. Although a system could be devised utilizing a higher repetition frequency, the added complexity needed to eliminate backscattering from previous transmissions would probably not be offset by any significant improvement in performance. It should be noted, however, that the water 12 is provided solely as a transmission medium. Thus any material capable of conveying ultrasound between the transducer 14 and sample holder 16 may be used. Furthermore, any distance between the transducer 14 and sample holder 16 may be selected by simply modifying the parameters of the signals generated by the pulse generator 60. In a commercial embodiment of the invention, a shorter distance than 30 cm may be desired.

Figure 5:
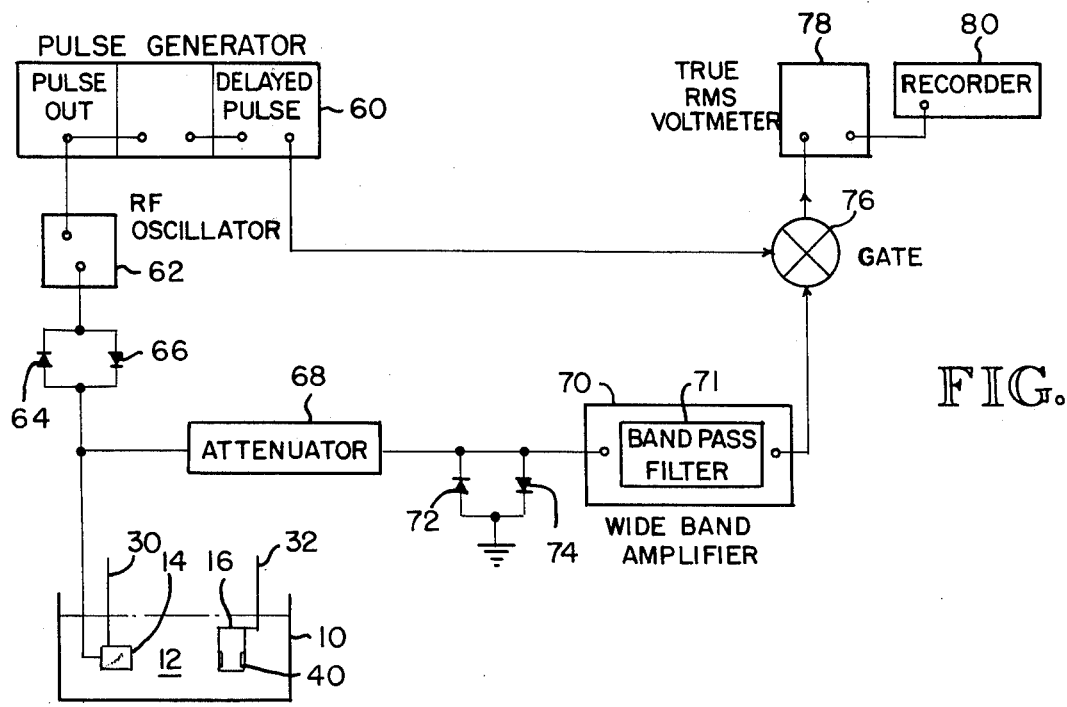
FIG. 5 is a schematic of the ultrasound coagulation timer of the present invention.

The electrical apparatus utilized to generate the waveform shown in FIG. 4A, as well as the system for receiving the backscattering, is shown in FIG. 5. A pulse generator 60, capable of generating a delayed pulse, is used to provide the basic timing. The pulse width is set to the desired width of the ultrasound burst $\tau$, and the delay is set to the round-trip transit time between the transducer 14 and sample holder 16. Any commercial pulse generator having these capabilities, such as Model 214A, manufactured by the Hewlett-Packard Company of Palo Alto, California, may be used. The non-delayed pulse from the pulse generator 60 is utilized to gate an rf oscillator 62, such as the Model FG-650 manufactured by the Arenberg Company of Boston, Massachusetts. The oscillator frequency is set to the desired frequency fc of the ultrasound burst. Thus, the waveform at the output of the oscillator 62 will be as shown in FIG. 4A. The oscillator 62 drives the transducer 14 through a pair of diodes arranged anode to cathode for the purpose of series thresholding. As will be explained hereinafter, the transducer 14 produces a low-level electrical signal upon detecting backscattering. This low-level signal would be greatly attenuated by the low-output impedance of the oscillator 62 if the oscillator 62 were connected directly to the transducer 14. Instead, the backscattering signal, which has a peak amplitude considerably less than the 0.7 volt diode drop of the silicon diodes 64, 66, is isolated from the oscillator 62 by the diodes 64, 66. However, the amplitude at the output of the oscillator 62 is of sufficient amplitude to forward bias the diodes 64, 66, thus driving the transducer 14.

The transmitted ultrasound propagates through the water 12 in the tank 10 and enters the aperture 40 in the sample holder 16 where it is backscattered by the whole blood or blood plasma sample contained therein. Since the backscattering from the blood sample begins when the first cycle of the ultrasound reaches the near surface of the sample holder and continues until the final cycle of the ultrasound reaches the far edge of the sample holder, the ultrasound backscattered from the sample has a width W twice the burst width $\tau$ of the transmitted ultrasound. However, the signal backscattered by the sample nearest the transducer is more intense than the signal backscattered by the sample farthest from the transducer. Since the more intense signal is closer to the transducer, it is received first. For this reason, the intensity of the backscattered ultrasound exponentially decays with time. This ultrasound backscattering signal arrives at the transducer 14 after a time delay D corresponding to the round-trip transit time between the transducer 14 and the sample holder 16. The backscattered signal at the output of the transducer 14 is shown in FIG. 4B. The signal includes, in addition to the backscattered ultrasound from the sample, signals of varying frequency produced by external sources as well as low-level ultrasound backscattered by the water and objects other than the sample. The backscattered signal from the transducer 14 passes through a calibration attenuator 68, such as the Kay Model 30-0 of Pinebrook, New Jersey. The attenuator 68 is adjustable to provide a predetermined output voltage at a given backscattering level. The attenuator 68 drives a wideband amplifier 70, such as the Keithley Model 106, through a line connected to ground through a pair of silicon diodes 72, 74 arranged anode to cathode. The diodes 72, 74 are voltage limiters to protect the sensitive input circuits of the wideband amplifier 70 from the high-amplitude ultrasound burst from the oscillator 62. However, the ultrasound backscattering signal is not attenuated by the diodes 72, 74 since the peak amplitude of that signal is considerably less than the 0.7 volt diode drop needed to forward bias the diodes 72, 74. The amplifier 70 contains a band pass filter 71 passing only the ultrasound frequency. The filter 71 greatly increases the signal-to-noise ratio of the signal at the output of the amplifier 70. As illustrated in FIG. 4C, the signal at the output of the amplifier 70 no longer contains the low-frequency components present at the input to the amplifier 70, as shown in FIG. 4B.

The output of the amplifier 70 is connected to a gate 76, such as a Relcom Mixer Model M1, operating over a frequency range of 0.2–500 MHz. The backscattering signal at the input to the gate 76 is conducted to the output by the delayed pulse from the pulse generator 60 which occurs a predetermined time after the ultrasound burst from the transducer 14. The gate 76, in combination with the delay circuit in the pulse generator 60, forms a range gate to enable measuring circuits to respond only to backscattering generated a predetermined distance from the transducer 14. In operation, the delay in the pulse generator 60 is set so that the delayed pulse from the pulse generator 60 occurs during the receipt of backscattering from the sample holder 16. Thus, the delay will be directly proportional to the distance from the transducer 14 to the sample holder 16 and back to the transducer 14. For example, in a system having the transducer 14 spaced 30 cm from the sample holder 16, the backscattering from the sample holder 16 is received at the transducer 14 420 $\mu s$ after the ultrasound burst was initiated. Thus the delayed pulse from the pulse generator 60 will occur approximately 420 microseconds after the undelayed pulse from the pulse generator 60 gates an ultrasound burst from the output of the oscillator 62. The delayed pulse is shown in FIG. 4D and the output of the gate 76 is shown in FIG. 4E. Note that the output from the gate 76 will be zero in the absence of a range gate pulse from the pulse generator 60.

The ultrasound backscattering signal at the output of the gate 76 drives a true RMS voltmeter 78, such as the Hewlett-Packard Model 3400-A. The output of the voltmeter 78 is shown in FIG. 4F and is a voltage proportional to the power of the signal at the input to the voltmeter 78. As mentioned earlier, a plurality of backscattering measurements will occur for each fluctuation of the backscattering characteristics of the whole blood or blood plasma sample in the sample holder 16. However, the voltmeter 78 is essentially a low-frequency device. Thus it will not respond to each individual backscattering measurement, but rather, it will respond to the average level of a number of backscattering measurements. This is desirable since the object of the system is to examine the fluctuations in amplitude of the backscattering and not to examine each of the plurality of individual backscattering measurements occurring during each fluctuation. The output of the RMS voltmeter 78, as shown in FIG. 4G, is displayed by a recorder 80 of conventional variety, such as the Model 291 by Linear Instruments Corp. of Irvine, California. Note that the first two relatively strong backscattering signals produce a relatively large signal at the output of the voltmeter 78, while the third backscattering measurement, which is taken substantially later, is of a somewhat lower amplitude, and thus produces a lower amplitude signal at the output of the voltmeter 78.

In the conventional thrombin test, the predetermined amount of thrombin added to the blood plasma is specified in NIH units of thrombin. One NIH unit is the quantity of thrombin that clots 1 ml of standard fibrinogen solution at 28° C. in 15 seconds. Since the unknown quantity is the quantity of fibrinogen in a given quantity of sample, and the known quantity is the thrombin time, a calibration curve is derived showing the relationship between thrombin time and fibrinogen concentration. However, presently existing calibration curves are for use with blood plasma, and not whole blood, and thus must be modified for measurements performed on whole blood. The thrombin time depends on the amount of fibrinogen F in the sample. The formula $F = 0.01\ fdC\ (1-H)$ defines the amount of fibrinogen in a sample of blood, where $f$ is the fibrinogen in mg/100 ml of plasma, $d$ is the dilution of the solution, C is the total volume of the sample in milliliters and H is the hematocrit. The hematocrit is the percentage by volume of the red cells to whole blood. For plasma and whole blood that have the same thrombin time, $0.01\ f_p\ d_p\ C_p = 0.01\ f_w\ d_w\ C_w\ (1-H)$, where p and w are subscripts indicating plasma and whole blood variables, respectively. Solving for $f_w$, $$f_w = \frac{f_p\ d_p\ C_p}{d_w\ C_w\ (1-H)}.$$

Figure 6:
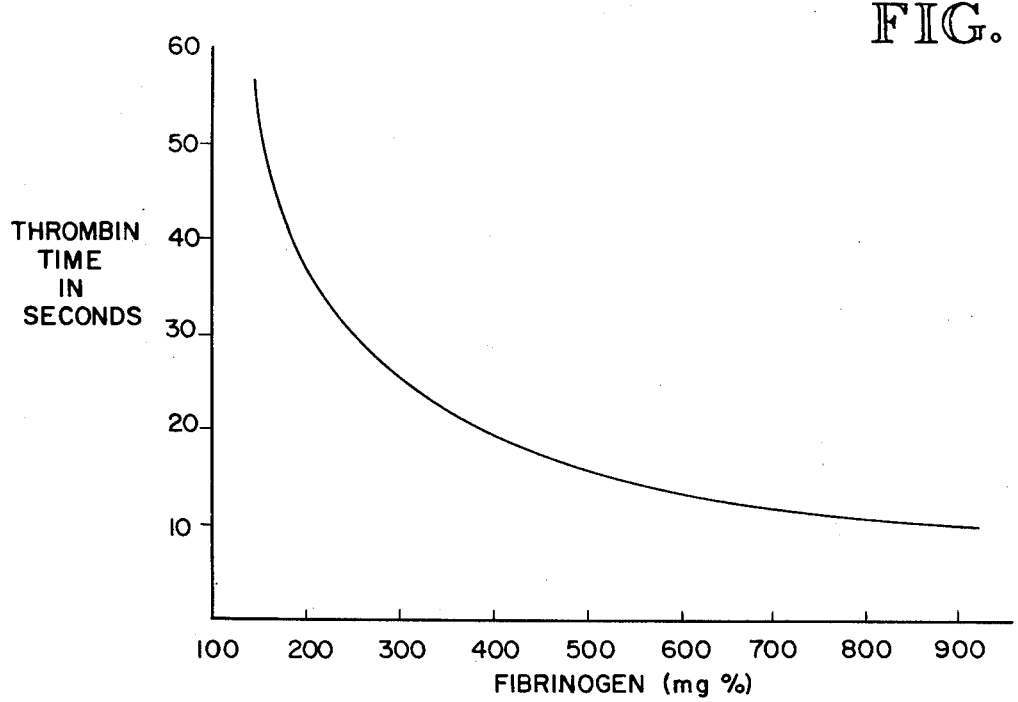
FIG. 6 is a calibration curve in which thrombin time is plotted as a function of fibrinogen quantity.

The quantity $f_p$ is known from calibration curves for plasma, when $C_p = C_w$ and $d_p = d_w, f_w = f_p/(1-H)$. Using this formula, a calibration curve for measuring the quantity of fibrinogen in a 2 ml sample of whole blood as a function of thrombin time may be obtained using calibration curves for blood plasma. Such a curve is shown in FIG. 6.

Figure 7:
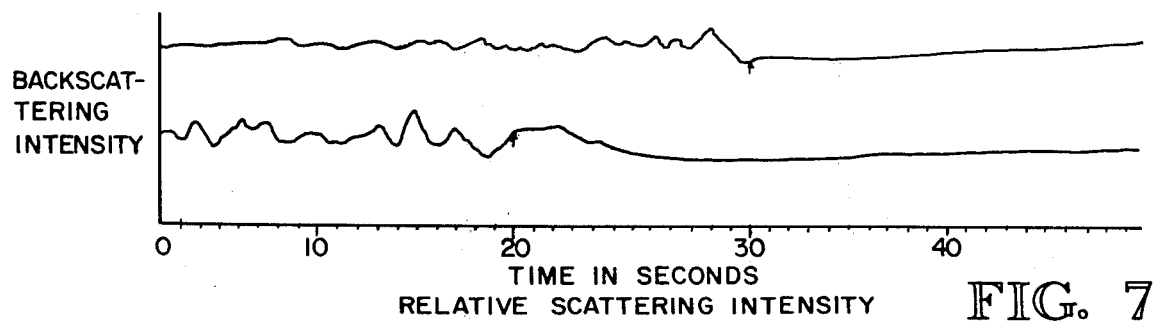
FIG. 7 is a graph in which the amplitude of the ultrasound backscattering is plotted as a function of time. The graph clearly shows the coagulation point for two different samples of blood.

Actual experimental results, as obtained by the recorder 80 (FIG. 5), are shown in FIG. 7. This graph shows the relative scattering intensity plotted as a function of time for two different blood samples. In the experimental procedure, 2 ml of a solution of whole blood or blood plasma is placed in the sample holder 16 and allowed to reach thermal equilibrium with the water in the tank. Then a pedetermined quantity of thrombin solution at 37° C. is added to the sample. The recorder 80 (FIG. 5) is actuated as soon as the thrombin solution is added to the sample. As shown by the graphs in FIG. 7, the scattering intensity fluctuates as soon as the thrombin solution is added and continues, in the case of the top curve, for 30 seconds. Referring to the calibration curve of FIG. 6, this indicates a fibrinogen concentration of approximately 240 mg/100 ml. The lower curve in FIG. 7 ceases fluctuating 18 seconds after the thrombin solution is added, thereby indicating a fibrinogen concentration of approximately 475 mg/100 ml.

Figure 8:
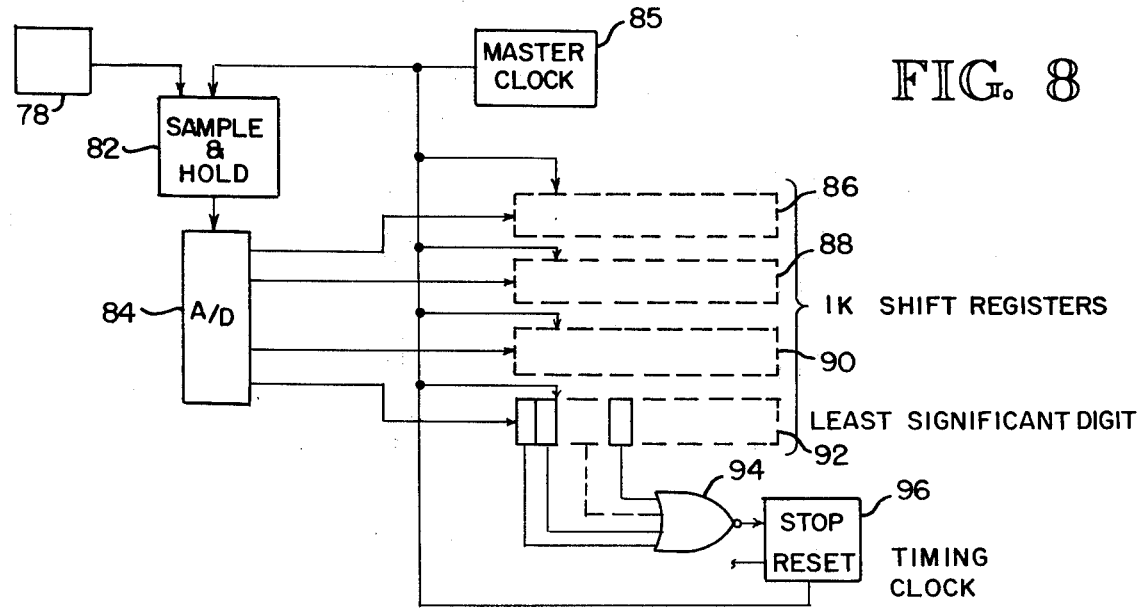
FIG. 8 is a schematic showing a circuit for digitally sampling and recording the amplitude of the ultrasound backscattering and for automatically signaling the incidence of coagulation.

In a commercial embodiment of the ultrasonic coagulation detector, it may be desired to measure the coagulation time without intervention from an operator. Furthermore, it may be desirable to obtain a graph representing the coagulation process which may contain information on abnormalities or other parameters of the coagulation process. The circuit shown in FIG. 8 may be used to perform both of these functions. In general, the thrombin time is less than 1 minute. A storage capability of 2 minutes and a sampling rate of 8 samples per second requires 960 storage spaces. Referring to FIG. 8, the timing for the system is provided by a master clock 85 having an output of 8 pulses per second. The output of the RMS voltmeter 78 (FIG. 5) drives a sample-and-hold circuit which produces a continuous output equal to the amplitude of the output of the voltmeter 78 at the instant of sampling. The sample-and-hold circuit 82 drives an analog-to-digital converter 84, feeding four 1,000-position shift registers 86, 88, 90, and 92, connected in parallel. The master clock 85 shifts each of the shift registers 86, 88, 90, 92 one digit for each sample of the output of the voltmeter 78. Thus, for each pulse of the master clock 85, the previous sample is shifted into the shift registers 86–92, and a new sample is gated to the output of the sample and hold 82. The last four samples contained in the shift register for the least significant digit 92 are continuously examined by NOR gate 94. When the least significant digit for any four successive samples is O, indicating that the backscattering signal has stabilized and hence the sample has coagulated, the output of the NOR gate 94 stops the timing clock 96 from incrementing. Timing clock 96 is driven by the master clock 85 and is reset to zero when the thrombin solution is added to the sample. Thus the digital output of the timing clock 96 indicates the elapsed time between addition of the thrombin solution and the stabilization of the backscattering signal. If desired, the output can be calibrated to read the concentration of fibrinogen in a sample. At the same time, the backscattering signal during the entire coagulation process is stored in the shift registers 86–92.

Since the ultrasound method is based on the principle that during biochemical reactions the interaction of ultrasound with the reagents changes, any assay which involves some biochemical reaction is a potential candidate for the ultrasound method. Thus, a wide variety of hematological tests and biochemical reactions may be monitored with the inventive system. Some of these hematological tests may include thromboelastography, quantitative hemoglobin in plasma and urine, osmotic fragility, mechanical fragility of erythrocytes, demonstration of sickle cells, A.B.O. blood grouping, RH, direct antiglobulin (Coombs), venous coagulation and clot retraction, and studies of the clot.

Using the ultrasonic coagulation timer of the present invention, the fibrinogen concentration can be quickly and easily determined from a sample of whole blood with a minimum of skill and expense.

The embodiments of the invention in which a particular property or privilege is claimed are defined as follows:

1. A method of measuring the coagulation time of a solution containing whole blood or blood plasma, comprising:
    directing ultrasound toward said solution and receiving the scattered ultrasound;
    mixing a predetermined quantity of thrombin witn said solution;
    examining the scattered ultrasound for an indication that said solution has coagulated; and
    measuring the elapsed tine between the mixing of thrombin with said solution and the coagulation of said solution.

2. The method of claim 1 wherein coagulation is indicated by a decrease in amplitude of fluctuations in scattering intensity.

3. The method of claim 1 wherein the received scattered ultrasound is converted into an electrical scattering signal indicative of the scattering intensity, said scattering signal being filtered to attenuate frequency components above a predetermined value, thereby obtaining an average scattering intensity signal.

4. The method of claim 3 wherein said average scattering intensity signal is continuously recorded during the period subsequent to mixing thrombin with the solution and prior to coagulation and wherein the recorded signal is examined for determining the presence of pathological coagulation.

5. The method of claim 4 wherein said pathological coagulation is indicated by a relatively indistinct indication of coagulation.

6. The method of claim 3 wherein said average scattering intensity signal is periodically sampled and converted to a binary coded signal corresponding to the amplitude of said sample and wherein the binary signal for each sample is digitally recorded.

7. The method of claim 6, further including the steps of:
    initiating the counting of periodically occurring pulses when said thrombin is mixed with said solution;
    examining the least significant digit of said binary coded signal for a plurality of successive samples; and
    terminating the counting of said periodically occurring pulses when all of said binary signals are a predetermined value.

8. The method of claim 1 wherein the step of directing ultrasound toward said solution comprises:
    transmitting a plurality of periodically occurring ultrasound bursts having a width approximately equal to the transit time of said ultrasound through said sample; and
    wherein said step or receiving the scattered ultrasound comprises:
    converting said ultrasound to an electrical signal indicative thereof;
    band pass filtering said electrical signal to attenuate all frequencies substantially different from the frequency of said ultrasound;
    applying the band pass filtered signal to a range gate, said range gate conducting a signal therethrough only during the occurrence of a range gate pulse, said range gate pulse occurring after the transmission of each ultrasound burst with a delay substantially equal to the time required for receiving scattered energy from each transmitted ultrasound burst;
    generating an output signal indicative of the intensity of said range gated signal; and
    sensing coagulation of said solution by examining said output signal for a change in amplitude of a fluctuating component of said output signal.

9. A method of detecting the termination of a biochemical reaction, comprising:
    irradiating an ultrasound, transparent sample holder with ultrasound, said sample holder holding a first chemical reactant;
    measuring the intensity of ultrasound scattering from the contents of said sample holder;
    adding a second chemical reactant to said sample holder; and
    sensing the occurrence of a marked decrease in amplitude of fluctuations in intensity of said ultrasound scattering.

10. An apparatus for measuring the coagulation time of a sample containing whole blood or blood plasma, comprising:
    an ultrasound-transmissive medium;
    a sample holder contained within said medium for receiving said sample, said sample holder having an ultrasound transparent window;
    an ultrasound transducer contained within said medium and adapted to direct ultrasound toward said sample holder and to receive ultrasound scattering therefrom;
    means for generating an ultrasound signal and driving said transducer with said signal; and
    means for receiving ultrasound scattering from the contents of said sample holder, said receiving means including means for measuring the intensity of said scattered ultrasound and for producing a signal indicative thereof.

11. The apparatus of claim 10 wherein said means for transmitting said ultrasound signal comprises:
    a pulse generator for periodically generating a first pulse;
    an ultrasound generator actuated in response to said first pulse whereby said ultrasound generator periodically generates an ultrasound burst; and
    said means for receiving ultrasound scattering comprises:
    a band pass filter for receiving a scattering signal from said transducer, said filter having a pass band centered at the ultrasound frequency whereby the signal-to-noise ratio of said scattering signal is improved; and
    means for producing an intensity signal having an amplitude indicative of the peak amplitude of said filtered ultrasound scattering signal.

12. The apparatus of claim 11 wherein said pulse generator produces a second pulse delayed from said first pulse by an amount substantially equal to twice the transit time of said ultrasound from said transducer to said sample holder and wherein said band pass filtered signal is applied to a range gate system including means responsive to said second pulse for conducting said signal to said means for producing an intensity signal.

13. The apparatus of claim 12, further including a low-pass filter for attenuating the frequency components in said intensity signal substantially above the frequency of intensity fluctuations in said scattering.

14. The apparatus of claim 11, further including means for digitally recording said intensity signal:
    a master clock;
    an analog-to-digital converter for generating a binary coded signal corresponding to the amplitude of said intensity signal; and
    a shift register responsive to said master clock for entering the output of said analog-to-digital converter into said shift register for each master clock pulse and for shifting previously centered binary coded signals one shift register stage for each master clock pulse.

15. The apparatus of claim 14, further including means for digitally indicating the thrombin time for a sample, comprising:
    a digital counter incremented by said master clock;

means for resetting said digital counter when thrombin is added to said sample;

means for examining a plurality of successive stages in said shift register containing the least significant digit of said binary coded signal; and means for disabling said digital counter when said examining means detects that said successive stages have identical numbers stored therein.

16. A method of measuring the coagulation time of a solution containing whole blood or blood plasma, comprising:

directing ultrasound toward said solution such that said ultrasound interacts with said solution;

receiving said ultrasound after interaction with said solution;

mixing a predetermined quantity of thrombin with said solution;

examining the received signal for a decrease in amplitude of fluctuations of said received signal responsive to coagulation of said solution; and measuring the elapsed time between the mixing of thrombin with said solution and the coagulation of said solution.

17. A method of detecting the termination of a biochemical reaction, comprising:

irradiating an ultrasound, transparent sample holder with ultrasound, said sample holder containing a first chemical reactant such that said ultrasound interacts with the contents of said sample holder;

adding a second chemical reactant to said sample holder;

receiving said ultrasound after interaction with the contents of said sample holder; and sensing the termination of said biochemical reaction by examining the received ultrasound for a decrease in amplitude of fluctuations of said received ultrasound responsive to termination of said reaction.

* * * * *